United States Patent [19]

Emanuel, deceased et al.

[11] 4,007,186
[45] Feb. 8, 1977

[54] PROCESS FOR PREPARING URIC ACID

[76] Inventors: Carl F. Emanuel, deceased, late of Bellevue, Wash.; Mary Victoria Emanuel, administratrix, 1025 156th NE., Bellevue, Wash. 98007

[22] Filed: Sept. 20, 1974

[21] Appl. No.: 507,728

[52] U.S. Cl. .............................................. 260/255
[51] Int. Cl.[2] ..................................... C07D 473/04
[58] Field of Search ................................... 260/255

[56] References Cited

UNITED STATES PATENTS 2,302,204  11/1942  Gable et al. ..................... 260/255

OTHER PUBLICATIONS

Kirk–Othmer, Encyclopedia of Chemical Technology, 2nd Ed., vol. 21 (1970) p. 109, Pub. by Wiley & Sons.

Primary Examiner—Paul M. Coughlan, Jr.
Attorney, Agent, or Firm—Robert B. Hughes

[57] ABSTRACT

A multi-faceted process for preparing uric acid of varying degrees of purity includes a first phase wherein uric acid of approximately 80–90% purity is prepared by dissolving fecal matter containing uric acid in a dilute alkali solution and then separating any undissolved solid residue therefrom. An ammonium salt is added to the solution to precipitate ammonium urate, which is readily convertible by conventional means to uric acid of 80–90% purity. Uric acid of even greater purity is prepared in the second phase by dissolving a relatively impure uric acid product, such as the above ammonium urate, in a second dilute alkali solution. Urate salt is then precipitated by gradually adjusting the pH of the second alkali solution with a dilute mineral acid to a pH of about 10.5. The urate salt is subsequently separated and converted to uric acid by suspending it in hot dilute mineral acid, the resultant uric acid having a purity of approximately 99%. The third phase of the present invention comprises preparing ultra pure crystalline uric acid by dissolving a relatively pure uric acid product, such as that obtained from the second phase, or an impure uric acid product, in a hot perchloric acid solution. Immediately upon dissolution of the uric acid, the hot perchloric acid solution is gradually cooled to form perchlorate salt crystals which contain uric acid. The perchlorate salt crystals are separated and then redissolved in a second hot perchloric acid solution which is thereupon immediately gradually cooled to again form perchlorate salt crystals containing uric acid. This second batch of perchlorate salt crystals is separated from the solution and then suspended in warm water to dissolve the perchloric acid and precipitate uric acid crystals. The resultant uric acid crystals are then separated and have a purity of approximately 99.9%.

18 Claims, 1 Drawing Figure

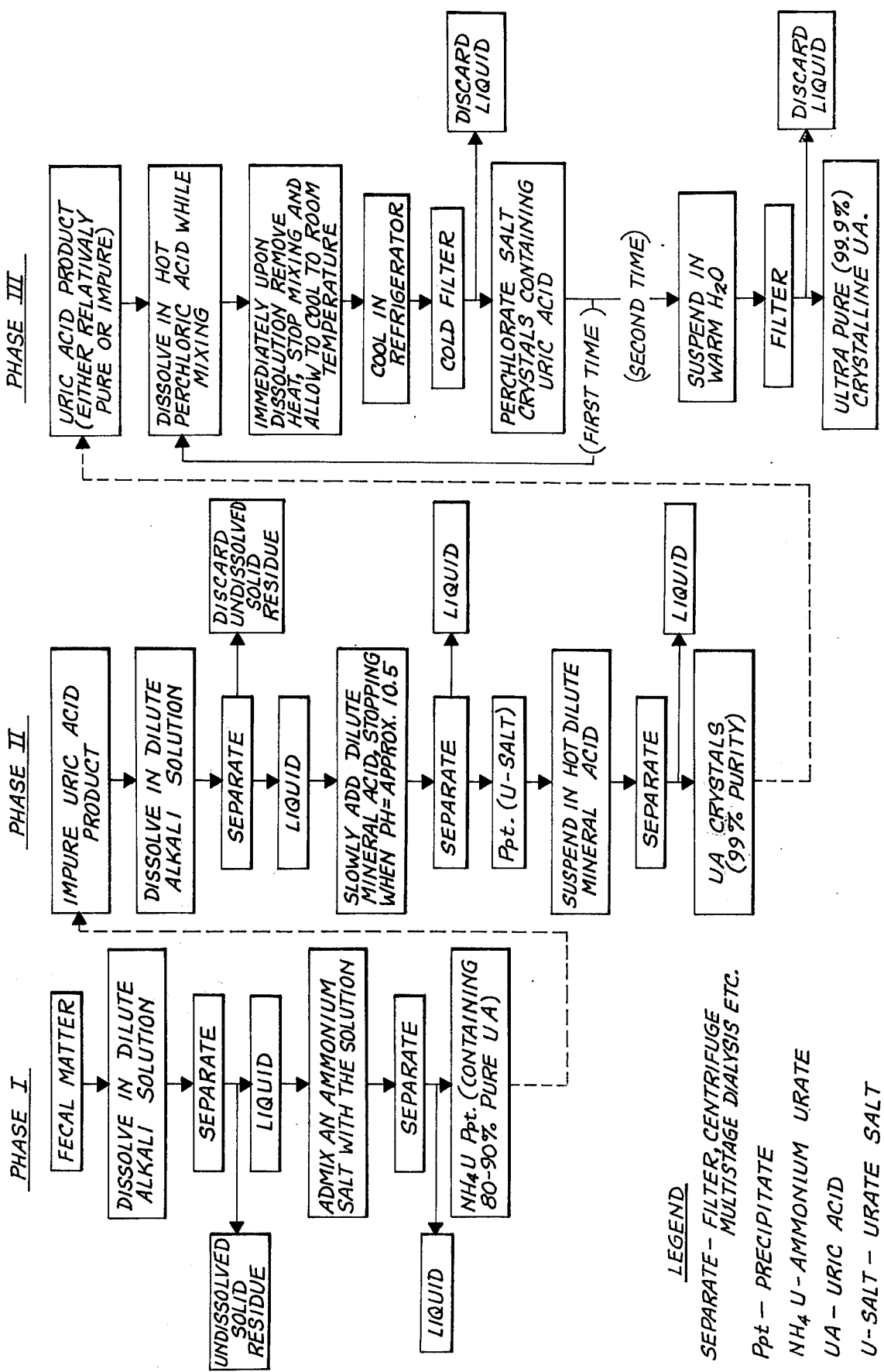

PROCESS FOR PREPARING URIC ACID

BACKGROUND OF THE INVENTION

1. Field of the Invention

This invention relates to a process of producing uric acid and more particularly to a multi-faceted process for producing uric acid of varying degrees of purity. Specifically, this invention relates to a process for producing increasingly pure quantities of uric acid from fecal matter containing uric acid.

2. Description of the Prior Art

Uric acid occurs in nature chiefly in the urinary excrement of animals, such as in marine guano, other bird feces and reptile feces. These materials are the main commercial sources of uric acid which is widely utilized in medical and university laboratories for studying and testing various human and animal diseases. In addition, uric acid is used in the synthesis of numerous other materials.

One of the chief difficulties in obtaining and purifying uric acid from such fecal matter has been the removal of certain highly colored pigments in addition to other trace contaminants. While known processes for purifying uric acid are generally acceptable for some of the above-enumerated purposes, uric acid of varying degrees of purity have different types of uses, and it would be highly desirable to have a single process capable of producing uric acid of various predetermined degrees of purity. In addition, no one has marketed a uric acid product or disclosed a method for producing a uric acid product which is sufficiently pure or crystalline to be capable of serving as an ideal reference standard.

German Pat. No. 462,353 discloses a process for purifying uric acid from marine guano by treating the fecal matter with a solution of water-soluble sulfides followed by filtering the uric acid after precipitation with mineral acid. Polish Pat. No. 47,019 discloses a somewhat different process for purifying uric acid from fecal matter by dissolving the fecal matter in a dilute base and then adding a reducing compound such as sodium sulfate. Separation of the uric acid is then accomplished by precipitating the uric acid with mineral acid, followed by washing and drying the product. Both of the above processes result in a considerable loss of uric acid and produce a uric acid product of insufficient purity to be utilized as a reference standard. Furthermore, none of the above patents disclose a single process for producing different degrees of uric acid purity.

U.S. Pat. No. 2,302,204 discloses an additional process for purifying uric acid from animal fecal matter. This process, however, merely utilizes a series of steps wherein the uric acid is alternately dissolved in a dilute alkali solution and then precipitated through the use of either mineral acid or by cooling the dilute alkali solution. Prior to the final step, the uric acid is dissolved once again in a dilute alkali solution which is then decolorized utilizing carbon. This process, as in the above-mentioned processes, basically utilizes well known steps and achieves a uric acid product which is insufficiently pure to serve as a reference standard.

SUMMARY OF THE INVENTION

It is, therefore, one object of the present invention to provide a process for purifying uric acid.

It is another object of the present invention to provide a multi-faceted process for producing uric acid of varying degrees of purity.

It is a further object of the present invention to provide a process for purifying uric acid from animal fecal matter, particularly poultry feces.

Yet another object of the present invention is to provide a process for producing ultra pure crystalline uric acid capable of serving as a reference standard.

To achieve the above and other objects and in accordance with the present invention, a crude uric acid product of approximately 80–90% purity is obtained by dissolving the appropriate animal fecal matter in a dilute alkali solution and separating any undissolved solid residue therefrom. This is preferably performed by vigorously mixing the fecal matter with the alkali solution under an inert atmosphere. The separated solid residue can be subsequently washed, sterilized and dried to form usable animal feed. An ammonium salt is then admixed with the alkali solution to precipitate ammonium urate, the ammonium salt preferably being in an excess amount thus affording virtually complete extraction of the uric acid from the fecal matter. The ammonium urate is then separated from the alkali solution to form the crude uric acid product.

While a uric acid product of 80–90% purity is useful in some instances, uric acid of greater purity is obtained in the second phase of the present invention by dissolving a relatively impure uric acid product, such as the ammonium urate from the first phase, in a second dilute alkali solution. Urate salt is then precipitated from this second alkali solution by gradually adjusting the pH of the solution with a dilute mineral acid, such as HCl, to a pH of about 10.5, at which point urate salt precipitates in large quantites. Further acidification of the solution to a pH below 10.5 is unnecessary and undesirable. The urate salt so formed is separated from this solution and suspended in a hot dilute mineral acid to convert the urate salt to uric acid. The uric acid precipitate is then separated and preferably washed and dried, resulting in a uric acid product which assays at approximately 99% purity.

To obtain ultra pure crystalline uric acid, a relatively pure uric acid product, such as that obtained from the second phase of the invention, or an impure uric acid product, is dissolved in a hot perchloric acid solution. Immediately upon dissolution of the uric acid in the perchloric acid, the perchloric acid solution is gradually cooled to form perchlorate salt crystals containing uric acid. The perchlorate salt crystals so formed are separated from the solution and then redissolved in a second hot perchloric acid solution. Immediately upon dissolution of the perchlorate salt crystals, the second perchloric acid solution is gradually cooled so as to again form perchlorate salt crystals containing uric acid. These perchlorate salt crystals are separated from the second perchloric acid solution and suspended in warm water to dissolve the perchloric acid and to precipitate uric acid crystals. The crystalline uric acid precipitate is then separated from the warm water solution and preferably washed with distilled water and dried with distilled, anhydrous methanol. The resulting uric acid crystals are ultra pure of approximately 99.9% purity while containing no fluorescent or ureide contaminants, and therefore they can serve as an ideal reference standard.

BRIEF DESCRIPTION OF THE DRAWING

The FIGURE is a general flow sheet showing the various facets or phases of the process for producing uric acid of varying degrees of purity according to the present invention.

DETAILED DESCRIPTION OF THE INVENTION

In practicing the present invention and with reference to the FIGURE, the first phase of the process includes dissolving fecal matter containing uric acid, such as poultry feces, in a dilute alkali solution and mixing vigorously therewith under an inert atmosphere. Preferably, the fecal matter is suspended for at least thirty minutes in a 2 to 5% triethylamine solution, although other basic salts can be utilized such as potassium hydroxide, lithium hydroxide, primary organic amines, secondary organic amines or other tertiary organic amines. In addition, while a nitrogen atmosphere is preferred, any inert atmosphere may be utilized. In this manner, the uric acid contained in the fecal matter, as well as other materials such as soluble proteins, inorganic salts and mucin, are extracted therefrom by the alkali solution while the solid residue containing phosphates and other beneficial ingredients for animal feed remains in suspension. This solution is then separated into a liquid phase and a solid phase by any known manner such as centrifugation, filtration or preferably by a multi-stage dialysis operation.

The liquid phase containing the solublized uric acid is then slowly mixed with an ammonium salt to precipitate ammonium urate. Preferably, an excess of the ammonium salt is utilized and is admixed with the filtered alkali solution for at least thirty minutes. Any ammonium salt such as $NH_4Cl$ may be utilized, although diammonium hydrogen phosphate, $(NH_4)_2HPO_4$, is preferred. The ammonium salt extracts virtually all of the uric acid from the solution. The ammonium urate precipitate is then separated from the solution and preferably washed with absolute methanol and then air dried. The white ammonium urate is a relatively impure uric acid product convertible by conventional processes to approximately 80-90% pure uric acid. The diammonium hydrogen phosphate gives a maximum yield and a superior ammonium urate product in terms of whiteness and composition.

In a continuous process, the fecal residue not dissolved by the alkali solution can be washed, sterilized and dried for refeeding to animals inasmuch as it contains useful and usable nutrients. In addition, the liquid separated from the ammonium urate can be used for recovery of other constituents therein or for biological conversion to food microbially and/or hydroponically. Furthermore, the methanol used for washing can be recovered, redistilled and reused.

While a uric acid product of 80-90% purity is useful for a number of purposes, it is often highly desirable to have a uric acid product of even greater purity. To obtain a purer uric acid product and in accordance with the second phase of the present invention, a relatively impure uric acid product, such as the separated ammonium urate previously mentioned, is dissolved in a second dilute alkali solution while mixing gently. This alkali solution is preferably potassium hydroxide, although any similar alkali solution such as those mentioned in the first phase of the present invention may be utilized. If any particles remain undissolved in the second alkali solution, the solution is preferably filtered through sintered glass. Urate salt is then precipitated from this second alkali solution by gradually adjusting the pH of the solution with a dilute mineral acid to a pH of about 10.5. Preferably, 2N hydrochloric acid is slowly added to the alkali solution while mixing vigorously. As the alkalinity of the solution decreases, urate salt gradually precipitates beginning at about pH 12.5. When the pH reaches about 10.5, the mixing and acidification is stopped, and the urate salt very quickly settles out and is readily filtered after decantation of the solution. The filtered urate salt is then preferably washed with distilled water, washed with absolute methanol and then finally dried in an air stream. It should be noted that acidification of this second alkali solution beyond a pH of about 10.5 is both unnecessary and undesirable.

The urate salt product so obtained is then suspended in a hot dilute mineral acid to convert the salt to uric acid. In preferred form, hot 0.1N perchloric acid is utilized. The uric acid precipitate is then filtered from the solution, washed and then dried at approximately 120° C. to remove any organic solvents which might remain due to the danger of possible explosion of such organic solvents, especially alcohol, should they come into contact with hot concentrated perchloric acid, as explained below. The uric acid product obtained from this facet of the present process assays at approximately 99% purity and is useful in many processes for synthesizing other materials as explained in more detail below.

In a continuous process, further quantities of a much more impure urate salt can be obtained from the second phase's filtered alkali solution if the acidity, after removal of the urate salt at pH 10.5, is then greatly increased until the pH reaches a value of about 1.3. The impure urate salt product which precipitates therefrom is amber in color and can be further purified by subjecting it to a repetition of the second phase of the present invention.

While a 99% pure uric acid product is quite useful in many processes, it is also desirable to obtain ultra pure crystalline uric acid to serve as a reference standard. To obtain such a highly pure uric acid product and with reference to the third phase of the present invention, a relatively pure uric acid product, such as the 99% pure uric acid obtained from the second phase of the present process, or other uric acid product such as sodium urate, whether relatively pure or impure, is dissolved in a hot perchloric acid solution. Perchloric acid is utilized in that it is so strong an acid, it brings forth the basic rather than the acidic properties of uric acid while destroying or carbonizing other organic impurities. No other common mineral acid functions in this manner.

Preferably, approximately 5 grams of the uric acid product are admixed with 50 cc of 70-73% vacuum distilled perchloric acid in a boiling water bath. Immediately upon dissolution of the uric acid, which takes approximately 5 to 10 minutes, an entirely clear solution results. When this occurs, mixing is immediately ceased, and the solution is then preferably filtered through a hot sintered disc and set aside, undisturbed, at room temperature for cooling and crystallization. It should be emphasized that the cessation of heating and mixing of the solution should occur immediately upon the complete dissolution of the uric acid to avoid any undue exposure of the uric acid to hot perchloric acid and thus prevent oxidative decomposition of the uric acid. Shortly after setting the solution aside at room temperature, an abundant mass of perchlorate salt starts to form as clear hexagonal plates. When this occurs, the solution is placed without mixing in a cold room or refrigerator. After several hours, the perchlorate salt crystals, which contain the uric acid, are filtered from the solution on a chilled sintered funnel and then preferably dried by sucking well-dried air over them.

The perchlorate salt crystals so obtained are then redissolved in a second similar hot perchloric acid solution, and immediately upon dissolution of the perchlorate salt crystals, the second perchloric acid solution is similarly set aside to cool to room temperature and then placed in a cold room or refrigerator to again form perchlorate salt crystals containing uric acid. After cooling, the perchlorate salt crystals are again filtered off on a chilled sintered funnel and dried by sucking air over them. These perchlorate salt crystals are subsequently suspended in a warm water solution to dissolve the perchloric acid and precipitate uric acid crystals. The crystalline uric acid is filtered from the warm water solution and preferably washed with distilled water and dried with distilled, anhydrous methanol. The resulting uric acid crystals assay at an ultra pure quality of approximately 99.9% and contain no fluorescent or ureide contaminants. Such an ultra pure uric acid product is capable of serving as an ideal reference standard.

If the ultra pure crystalline uric acid is to be utilized as a reference standard, it may be desirable to further assure oneself of the purity of the product, especially if a relatively impure uric acid product was utilized in the beginning of the third phase. To achieve this, the 99.9% ultra pure crystalline uric acid obtained from the third phase of the present process is dissolved in dilute, twice distilled triethylamine. This solution is heated and then acidified with excess pure perchloric acid (70% solution). The acidified triethylamine solution is then set aside undisturbed at room temperature and allowed to cool, after which it is placed into a cold room or refrigerator for further cooling. The uric acid crystals which form in this solution are then filtered and preferably washed with glass distilled water and glass distilled methanol to yield ultra pure crystalline uric acid with negligible ash. If one wishes to obtain the 99.9% ultra pure crystalline uric acid in a highly crystalline form, the 99.9% ultra pure uric acid crystals, or the second batch of perchlorate salt crystals containing the uric acid, from the third phase of the present invention are suspended in glass distilled water containing an effective amount of saturated (carbonate-free) sodium hydroxide to dissolve the uric acid. This solution is then diluted to approximately two liters, heated to boiling and acidified with excess pure perchloric acid (70% solution). This solution is then set aside at room temperature to cool, after which it is placed into a cold room or refrigerator for further cooling. The resultant uric acid precipitate is filtered from this solution and preferably washed with glass distilled water and glass distilled methanol. This results in ultra pure uric acid in the form of very large crystals.

The following examples are illustrative of the invention but are not intended to be limiting in any manner.

EXAMPLE I

Fifteen grams of dried chicken feces were admixed with three parts of 2.5% potassium hydroxide under an inert atmosphere and cooked for two days. The solid, undissolved residue portion was then centrifuged off and washed with an equal volume of water. The wash water was combined with the liquid alkali solution and then admixed with an excess amount of diammonium hydrogen phosphate. This solution was allowed to stand for approximately two hours while a white granular ammonium urate precipitate formed. The ammonium urate precipitate was then centrifuged, separated from the liquid, washed with an equal volume of water, washed with three volumes of absolute methanol and then washed with ether. 1.61 grams of dry weight ammonium urate was obtained thus forming a crude (80–90% pure) uric acid product.

EXAMPLE II

To form an even purer uric acid product, five grams of a relatively impure uric acid product, such as the ammonium urate from Example I or in this particular case Eastman Kodak uric acid, were dissolved in 200 cc of 2% potassium hydroxide followed by a further addition of 19N sodium hydroxide at 100° C. This solution was then gently mixed, filtered to remove any undissolved solid residue and then cooled.

With the pH of the solution initially being about 13.0, a 2.4N hydrochloric acid solution was slowly titrated into the filtered alkali solution while mixing vigorously until the solution had a persistent cloudiness at about a pH of 12.3. The titration was then continued to a pH of approximately 12.0 followed by stirring without further titration for about five minutes, which returned the pH to about 12.4. A urate salt precipitated out at once resulting in a clear yellow supernate. This urate salt precipitate was filtered from the solution, washed with water and methanol and then dried to produce 1.4 grams of a urate salt product. Acidification of the clear yellow supernate with the hydrochloric acid was then continued until a pH of about 11.0 was obtained. At this point, acidification was stopped, and the resultant precipitate was filtered to give a very white urate salt product and a yellow supernate. The urate salt precipitate was then washed and dried as above to produce 3.9 grams of urate salt product. This urate salt can be readily converted to uric acid as heretofore explained, the resulting uric acid having a purity of approximately 99%.

EXAMPLE III

To obtain ultra pure crystalline uric acid, 5 grams of Eastman Kodak uric acid were dissolved at 100° C. in 66 cc of 72% perchloric acid. It should be noted, however, that the 99% pure uric acid from Example II could have been utilized in lieu of the Eastman Kodak uric acid. Prior to the dissolution in the perchloric acid, the uric acid was finely ground to avoid lumps which prolong dissolution in the perchloric acid and thereby increase the exposure time, which is to be avoided. The suspension was vigorously mixed during heating to minimize exposure of the uric acid to the hot perchloric acid. When all the uric acid had dissolved, the yellow solution was quickly filtered through a hot sintered disc, rewarmed, and then set aside at room temperature. Very quickly a coarse crystalline deposit began to form, and when the solution reached room temperature, it was placed in a refrigerator for further cooling. The pure white perchlorate salt crystals, containing uric acid, were then filtered from the cooled solution on sintered glass and sucked very dry with air. These crystals were redissolved at 100° C. in 50–60 cc 72% perchloric acid, and when the perchlorate salt crystals had completely dissolved, the second perchloric acid solution was set aside and cooled as described above. The resulting crystals from the second perchloric acid solution were large hexagonal plates which could be decomposed with water, thereby yielding a uric acid precipitate. Chromatography showed that the uric acid so obtained was pure with no fluorescent or ureide contaminants.

As can be seen from the above, the subject invention is a highly efficient yet relatively simple process for producing uric acid of varying degrees of purity from fecal matter. The uric acid so produced, depending on the purity thereof, can be processed subsequently to produce a variety of drugs, chemicals, plastics and adhesives including cyanuric acid, from which melamine can be produced for use in making melamine resin plastic. In addition, the more pure forms of the uric acid can be utilized in the production of barbituric acid, dialuric acid, violuric acid, alloxantin, alloxan, parabanic acid, biuret, purpuric acid, hydurilic acid, allantoic acid, allantoin and urea. Furthermore, the ultra pure crystalline uric acid obtained from the final facet of the present process, while it may be utilized to produce the above substances, can also be utilized as an ideal reference standard for measuring the degrees of purity of other uric acid products. Such a standard of the disclosed purity has not heretofore been produced.

It will be understood that the invention may be embodied in other specific forms without departing from the spirit or central characteristics thereof. The present examples and embodiments, therefore, are to be considered in all respects as illustrative and not restrictive, and the invention is not to be limited to the details given herein but may be modified within the scope of the appended claims.

What is claimed is:

1. A process of preparing ultra pure crystalline uric acid comprising dissolving a uric acid product in a first hot perchloric acid solution, gradually cooling said perchloric acid solution upon dissolution of said uric acid product to form perchlorate salt crystals containing uric acid, separating the perchlorate salt crystals from said solution, redissolving the perchlorate salt crystals in a second hot perchloric acid solution, cooling said second perchloric acid solution upon dissolution of said perchlorate salt crystals to again form perchlorate salt crystals containing uric acid, separating the perchlorate salt crystals obtained from the second perchloric acid solution, suspending said separated perchlorate salt crystals in a warm water solution to dissolve the perchloric acid and precipitate uric acid crystals, and separating said uric acid crystals from said warm water solution thereby obtaining ultra pure crystalline uric acid.

2. The process according to claim 1, wherein said uric acid product is dried at approximately 120° C. prior to dissolution in said first hot perchloric acid solution to remove any organic solvents contained therein.

3. The process according to claim 2, wherein said dried uric acid product is dissolved in said first hot perchloric acid solution by vigorously admixing the uric acid product with the perchloric acid for approximately five to ten minutes, additional mixing time and exposure of the uric acid to hot perchloric acid being avoided to prevent oxidative decomposition of said uric acid.

4. The process according to claim 1, wherein said perchlorate salt crystals containing uric acid are dissolved in said second hot perchloric acid solution by vigorously admixing said crystals with the perchloric acid for approximately five to ten minutes, additional mixing time and exposure of the uric acid contained in said crystals to hot perchloric acid being avoided to prevent oxidative decomposition of said uric acid.

5. The process according to claim 1, wherein said hot perchloric acid solutions containing dissolved uric acid are immediately hot filtered upon complete dissolution of the solute, set aside to cool undisturbed to room temperature, and then placed in a cold room to cool below room temperature.

6. A process of preparing ultra pure crystalline uric acid from fecal matter containing uric acid comprising:
dissolving said fecal matter in a dilute alkali solution and separating any undissolved solid residue therefrom;
admixing an ammonium salt with said alkali solution to precipitate ammonium urate;
separating the ammonium urate precipitate from said solution and dissolving said ammonium urate in a second dilute alkali solution;
precipitating urate salt from said second alkali solution by gradually adjusting the pH of said solution with dilute mineral acid to a pH of about 10.5;
separating the precipitated urate salt from said solution and suspending said urate salt in hot dilute mineral acid to precipitate uric acid;
separating said uric acid precipitate;
dissolving said separated uric acid precipitate in a first hot perchloric acid solution and immediately gradually cooling said perchloric acid solution to form perchlorate salt crystals containing uric acid;
separating the perchlorate salt crystals from said solution;
redissolving said perchlorate salt crystals in a second hot perchloric acid solution and immediately gradually cooling said second perchloric acid solution to again form perchlorate salt crystals containing uric acid;
separating the perchlorate salt crystals obtained from said second perchloric acid solution;
suspending said separated perchlorate salt crystals in a warm water solution to dissolve the perchloric acid and precipitate uric acid crystals; and
separating the uric acid crystals from said warm water solution to obtain ultra pure crystalline uric acid.

7. The process according to claim 6, wherein said ammonium salt is diammonium hydrogen phosphate.

8. The process according to claim 6, wherein said dilute alkali solutions are selected from the group consisting of potassium hydroxide, lithium hydroxide, sodium hydroxide, primary amines, secondary amines and tertiary amines.

9. The process according to claim 6, wherein the pH of said second alkali solution is adjusted by slowly adding approximately 2N hydrochloric acid, and wherein said urate salt precipitate is suspended in hot dilute perchloric acid to precipitate said uric acid.

10. The process according to claim 6, wherein said uric acid precipitate is dried at approximately 120° C. prior to dissolution in said first hot perchloric acid solution to remove any organic solvents contained therein.

11. The process according to claim 10, wherein said dried uric acid precipitate is dissolved in said first hot perchloric acid solution by vigorously admixing said uric acid with said perchloric acid for approximately five to ten minutes, additional mixing time and exposure of the uric acid to hot perchloric acid being avoided to prevent oxidative decomposition of the uric acid.

12. The process according to claim 6, wherein said perchlorate salt crystals are dissolved in said second hot perchloric acid solution by vigorously admixing said crystals with the perchloric acid for approximately five to ten minutes, additional mixing time and exposure of the uric acid contained in said crystals to hot perchloric acid being avoided to prevent oxidative decomposition of the uric acid.

13. The process according to claim 6, wherein said ultra pure crystalline uric acid is further purified by dissolving said ultra pure crystalline uric acid in a solution of dilute, twice-distilled triethylamine, heating said solution, acidifying said solution with excess perchloric acid, slowly cooling said solution to form crystalline uric acid precipitate, filtering the solution, washing the filtered uric acid precipitate with glass distilled water, and washing said uric acid precipitate with glass distilled methanol to obtain ultra pure crystalline uric acid with negligible ash.

14. The process according to claim 6, wherein said ultra pure crystalline uric acid is converted to highly crystalline ultra pure uric acid by suspending said ultra pure uric acid in distilled water containing an effective amount of saturated, carbonate-free sodium hydroxide to dissolve said uric acid, diluting the solution, heating the solution to boiling, acidifying said solution with excess perchloric acid, slowly cooling said solution to form uric acid crystals, filtering said solution, washing the filtered uric acid crystals with glass distilled water, and washing said crystals with glass distilled methanol to obtain highly crystalline ultra pure uric acid.

15. The process according to claim 6, wherein the undissolved solid residue separated from the dilute alkali solution wherein said fecal matter is dissolved is washed, sterilized, and dried to form animal feed.

16. A process of purifying uric acid comprising dissolving an impure uric acid product in a dilute alkali solution, precipitating urate salt from said alkali solution by gradually adjusting the pH of said solution with dilute mineral acid to a pH of about 10.5, separating the urate salt precipitate from said solution, suspending said separated urate salt in hot dilute mineral acid to precipitate uric acid, and separating said uric acid precipitate from said mineral acid solution; then further purifying said uric acid precipitate by dissolving said uric acid precipitate in a first hot perchloric acid solution, gradually cooling said perchloric acid solution upon dissolution of said uric acid precipitate to form perchlorate salt crystals containing uric acid, separating the perchlorate salt crystals from said solution, redissolving said perchlorate salt crystals in a second hot perchloric acid solution, cooling said second perchloric acid solution upon dissolution of said perchlorate salt crystals to again form perchlorate salt crystals containing uric acid, separating the perchlorate salt crystals obtained from the second perchloric acid solution, suspending said separated perchlorate salt crystals in a warm water solution to dissolve the perchloric acid and precipitate uric acid crystals, and separating said uric acid crystals from said warm water solution thereby obtaining ultra pure crystalline uric acid.

17. The process according to claim 16, wherein said dilute mineral acid comprises hydrochloric acid.

18. A process of separating and purifying uric acid from fecal matter containing uric acid comprising dissolving the fecal matter in a dilute alkali solution, separating any undissolved solid residue from said alkali, admixing an ammonium salt with said alkali solution to precipitate ammonium urate, and separating the ammonium urate precipitate from said solution, said ammonium urate constituting a crude uric acid product, said uric acid being further purified by dissolving said ammonium urate in a second dilute alkali solution, precipitating urate salt from said second alkali solution by gradually adjusting the pH of said solution with dilute mineral acid to a pH of about 10.5, separating the precipitated urate salt from said solution, suspending said urate salt in hot dilute mineral acid to precipitate uric acid, and separating the uric acid precipitate from said mineral acid solution, said uric acid being yet further purified by dissolving said uric acid precipitate in a first hot perchloric acid solution, gradually cooling said perchloric acid solution upon dissolution of said uric acid precipitate to form perchlorate salt crystals containing uric acid, separating the perchlorate salt crystals from said solution, redissolving said perchlorate salt crystals in a second hot perchloric acid solution, cooling said second perchloric acid solution upon dissolution of said perchlorate salt crystals to again from perchlorate salt crystals containing uric acid, separating the perchlorate salt crystals obtained from the second perchloric acid solution, suspending said separated perchlorate salt crystals in a warm water solution to dissolve the perchloric acid and precipitate uric acid crystals, and separating said uric acid crystals from said warm water solution to dissolve the perchloric acid and precipitate uric acid crystals, and separating said uric acid crystals from said warm water solution thereby obtaining ultra pure crystalline uric acid.

* * * * *